(12) United States Patent
Song et al.

(10) Patent No.: US 10,828,209 B2
(45) Date of Patent: Nov. 10, 2020

(54) SOFT NONWOVEN FABRIC AND METHOD OF MANUFACTURING THEREOF

(71) Applicant: AVINTIV Specialty Materials Inc., Charlotte, NC (US)

(72) Inventors: Yiyin Song, Jiangsu (CN); Yisong Huo, Jiangsu (CN); Kang Zhen Chen, Foshan (CN); Chusheng Li, Foshan (CN)

(73) Assignee: AVINTIV Specialty Materials Inc., Charlotte, NC (US)

( * ) Notice: Subject to any disclaimer, the term of this patent is extended or adjusted under 35 U.S.C. 154(b) by 118 days.

(21) Appl. No.: 15/375,375

(22) Filed: Dec. 12, 2016

(65) Prior Publication Data

US 2017/0175313 A1  Jun. 22, 2017

Related U.S. Application Data

(60) Provisional application No. 62/268,194, filed on Dec. 16, 2015.

(51) Int. Cl.
| | | |
|---|---|---|
| *A61F 13/511* | (2006.01) | |
| *D04H 1/46* | (2012.01) | |
| *D04H 5/06* | (2006.01) | |
| *B31F 1/07* | (2006.01) | |
| *D04H 3/16* | (2006.01) | |

(Continued)

(52) U.S. Cl.
CPC ...... *A61F 13/51104* (2013.01); *A61F 13/511* (2013.01); *B31F 1/07* (2013.01); *D04H 1/46* (2013.01); *D04H 1/54* (2013.01); *D04H 3/14* (2013.01); *D04H 3/16* (2013.01); *D04H 5/06* (2013.01); *B31F 2201/0733* (2013.01); *B31F 2201/0756* (2013.01); *B31F 2201/0789* (2013.01)

(58) Field of Classification Search
CPC ....... Y10T 428/24826; Y10T 156/1023; A61F 13/51104; A61F 13/51108
See application file for complete search history.

(56) References Cited

U.S. PATENT DOCUMENTS

| | | |
|---|---|---|
| 3,616,157 A | 10/1971 | Smith |
| 3,855,046 A | 12/1974 | Hansen et al. |
| 3,973,068 A | 8/1976 | Weber |

(Continued)

FOREIGN PATENT DOCUMENTS

| | | |
|---|---|---|
| CL | 199692133 | 8/1997 |
| EP | 1322806 B1 | 9/2005 |

(Continued)

OTHER PUBLICATIONS

Full manual translation of JP S57/167442A (Year: 2019).*

(Continued)

*Primary Examiner* — Z. Jim Yang
(74) *Attorney, Agent, or Firm* — Burr & Forman LLP

(57) ABSTRACT

Fabrics having a desirable softness and exhibiting a low lint level are provided. The fabrics include an embossed bonding pattern, in which the embossed bonding pattern includes a plurality of icons (e.g., geometric shapes, caricatures, etc.). The plurality of icons may be defined by a plurality of perimeter bonding points. Additionally, from 1 to about 10 internal bonding points may be located within at least one of the plurality of icons.

18 Claims, 4 Drawing Sheets

(51) Int. Cl.
*D04H 1/54* (2012.01)
*D04H 3/14* (2012.01)

(56) References Cited

U.S. PATENT DOCUMENTS

| | | | |
|---|---|---|---|
| 4,091,137 A | 5/1978 | Miller | |
| 4,741,941 A | 5/1988 | Englebert et al. | |
| 5,009,651 A * | 4/1991 | Kamishioiri | A61F 13/5116 604/378 |
| 5,370,764 A * | 12/1994 | Alikhan | A61F 13/5116 156/553 |
| 5,424,115 A | 6/1995 | Stokes | |
| 5,620,779 A * | 4/1997 | Levy | D04H 1/544 428/167 |
| 5,858,515 A | 1/1999 | Stokes et al. | |
| 5,964,742 A | 10/1999 | McCormack et al. | |
| 5,993,714 A | 11/1999 | Sawyer et al. | |
| 6,093,665 A | 7/2000 | Sayovitz et al. | |
| 6,319,239 B1 * | 11/2001 | Daniels | A61F 13/539 604/378 |
| 6,361,784 B1 | 3/2002 | Brennan et al. | |
| D463,137 S | 9/2002 | Monroe et al. | |
| 6,537,644 B1 | 3/2003 | Kauschke et al. | |
| 6,610,390 B1 * | 8/2003 | Kauschke | B32B 5/26 428/198 |
| 6,638,605 B1 * | 10/2003 | Ankuda, Jr. | A41D 13/1209 428/198 |
| 6,752,947 B1 | 6/2004 | Lanigan et al. | |
| 6,986,825 B1 * | 1/2006 | Squires | B32B 7/04 156/209 |
| D516,318 S | 3/2006 | Hasenoehrl et al. | |
| D516,319 S | 3/2006 | Hasenoehrl et al. | |
| 7,914,723 B2 | 3/2011 | Kim et al. | |
| D702,047 S * | 4/2014 | Rhodes, III | D04H 1/559 D5/58 |
| 9,096,961 B2 | 8/2015 | Jones et al. | |
| D738,632 S * | 9/2015 | Seitzinger | D04H 1/541 D5/57 |
| D747,887 S * | 1/2016 | Seitzinger | A44B 18/0011 D5/57 |
| D773,833 S * | 12/2016 | Hannen | D5/57 |
| D777,451 S * | 1/2017 | Hunt | B26F 1/26 D5/2 |
| 10,132,042 B2 * | 11/2018 | Maladen | D21H 27/42 |
| 2003/0041953 A1 | 3/2003 | Farell et al. | |
| 2004/0241399 A1 * | 12/2004 | Marmon | D04H 13/00 428/196 |
| 2004/0267220 A1 * | 12/2004 | Hull, Jr. | A61F 13/51121 604/380 |
| 2005/0148260 A1 | 7/2005 | Kopacz et al. | |
| 2005/0159063 A1 | 7/2005 | Hill et al. | |
| 2005/0241088 A1 | 11/2005 | Brunner et al. | |
| 2006/0063456 A1 | 3/2006 | Carter | |
| 2006/0113049 A1 * | 6/2006 | Knobloch | D21H 27/30 162/117 |
| 2006/0169301 A1 * | 8/2006 | Haskett | A47L 13/16 134/6 |
| 2006/0286885 A1 * | 12/2006 | Schuh | D21H 25/005 442/327 |
| 2007/0087169 A1 * | 4/2007 | McFall | A61F 13/51394 428/172 |
| 2007/0130713 A1 | 6/2007 | Chen et al. | |
| 2007/0256803 A1 * | 11/2007 | Sheehan | D21H 27/005 162/123 |
| 2008/0182048 A1 | 7/2008 | Ouellette et al. | |
| 2009/0188090 A1 * | 7/2009 | Munstermann | B26F 1/26 28/104 |
| 2009/0297781 A1 * | 12/2009 | Huss | D21H 27/30 428/166 |
| 2010/0305543 A1 * | 12/2010 | Klaska | A61F 13/51401 604/391 |
| 2011/0223381 A1 * | 9/2011 | Sauter | B31F 1/07 428/131 |
| 2011/0244749 A1 * | 10/2011 | Fujiwara | D04H 1/54 442/394 |
| 2011/0319846 A1 * | 12/2011 | Rinnert | A61F 13/51496 604/366 |
| 2012/0059343 A1 * | 3/2012 | Kume | B29C 65/02 604/379 |
| 2012/0244320 A1 * | 9/2012 | Sauter | D21H 27/002 428/156 |
| 2012/0315440 A1 * | 12/2012 | Ichikawa | D04H 3/14 428/156 |
| 2013/0236700 A1 * | 9/2013 | Yamanaka | A61F 13/5116 428/169 |
| 2013/0260111 A1 * | 10/2013 | Kelsey | B32B 27/00 428/197 |
| 2013/0280481 A1 * | 10/2013 | Mitsuno | D04H 5/06 428/131 |
| 2013/0316135 A1 * | 11/2013 | Rawat | A61F 13/472 428/138 |
| 2014/0044934 A1 * | 2/2014 | Bills | A61F 13/51496 428/196 |
| 2014/0263033 A1 * | 9/2014 | Fu | D04H 3/14 210/500.1 |
| 2015/0001783 A1 * | 1/2015 | Gann-Fetter | B31F 1/07 270/58.3 |
| 2015/0086760 A1 * | 3/2015 | Castillo | D04H 1/485 428/198 |
| 2017/0014280 A1 * | 1/2017 | Moritani | A61F 13/51104 |
| 2017/0027774 A1 * | 2/2017 | Ashraf | A61F 13/55115 |
| 2017/0151101 A1 * | 6/2017 | Isele | D04H 1/74 |
| 2017/0151102 A1 * | 6/2017 | Isele | A61F 13/51121 |
| 2019/0161897 A1 * | 5/2019 | Mecl | D04H 3/14 |

FOREIGN PATENT DOCUMENTS

| | | | |
|---|---|---|---|
| GB | 2031039 A | | 4/1980 |
| JP | 57167442 A | * | 10/1982 |
| WO | 1998027257 A2 | | 6/1998 |
| WO | 1998055295 A1 | | 12/1998 |
| WO | 2002048440 A2 | | 6/2002 |
| WO | 2006004871 A1 | | 1/2006 |
| WO | 2008066417 A1 | | 6/2008 |
| WO | 2010066284 A1 | | 6/2010 |

OTHER PUBLICATIONS

International Search Report and Written Opinion of corresponding International Application No. PCT/US2016/066095 dated Mar. 22, 2017.

* cited by examiner

SOFT NONWOVEN FABRIC AND METHOD OF MANUFACTURING THEREOF

PRIORITY CLAIM

This application claims priority under 35 U.S.C. § 119(e) to U.S. Provisional Application Ser. No. 62/268,194, filed on Dec. 16, 2015, which is expressly incorporated by reference herein in its entirety.

TECHNICAL FIELD

The presently-disclosed invention relates generally to soft nonwoven fabrics having an embossed bonding pattern including a plurality of icons defined by a plurality of perimeter bonding points and at least one bonding point located within, for example, each of the plurality of icons.

BACKGROUND

A variety of commercial applications for nonwoven fabrics require abrasion resistance/low-linting while retaining a certain level of softness. By way of example, spunbond nonwoven fabrics have been widely used as various types of everyday items or industrial materials because they have desirable mechanical properties, such as tensile strength, due to the fact that they are formed from continuous fibers.

Of the various types of spunbond nonwoven fabrics available, those made of a polyamide or a polyester exhibit a relatively high softness. Therefore, attempts have been made to use them as materials which make direct contact with the human body, such as in disposable sheets or the top sheets of diapers. However, spunbond filaments forming spunbond nonwoven fabrics, by virtue of their method of formation, must be subjected to a bonding operation to hold the individual filaments together. Bonding operations may facilitate or improve the fabric's abrasion resistance, but may also negatively impact the level of softness of the fabric.

Therefore, there at least remains a need in the art for embossed nonwoven fabrics which exhibit a desirable softness to touch while retaining a desired level of abrasion resistance/low-linting.

SUMMARY OF INVENTION

One or more embodiments of the invention may address one or more of the aforementioned problems. Certain embodiments according to the invention provide fabrics comprising a nonwoven web including an embossed bonding pattern. The embossed bonding pattern, according to certain embodiments of the invention, may comprise a plurality of icons, in which each of the plurality of icons may be defined by a plurality of perimeter bonding points and from 1 to about 5 (e.g., 1-3) internal bonding points located within at least one of the plurality of icons. In certain embodiments of the invention, each of the icons include from 1 to about 5 internal bonding points located therein. Fabrics according to certain embodiments of the invention may comprise a plurality of icons, in which each of the plurality of icons comprise the same geometric shape. In certain other embodiments of the invention, the plurality of icons may comprise two or more different geometric shapes. In this regard, the embossed bonding pattern of fabrics, in accordance with certain embodiments of the invention, may comprise a plurality of different geometric shapes. Regardless of whether to plurality of icons of the embossed bonding pattern are all the same or not, the plurality of icons may each comprise an icon area from about 1 mm$^2$ to about 50 mm$^2$ (e.g., from about 1 mm$^2$ to about 25 mm$^2$). In this regard, each of the plurality of icons may have the same or different icon area. In accordance with certain embodiments of the invention, for example, the plurality of icons may include a first group of icons (e.g., including a first icon) comprising a first icon area and a second group of icons (e.g., including a second icon) comprising a second icon area, in which the first icon area is different than the second icon area. For example, the plurality of icons may comprise a first icon comprising a first icon area and a second icon comprising a second icon area, in which the first icon area is different than the second icon area.

In accordance with certain embodiments of the invention, each of the plurality of perimeter bonding points may comprise an individual perimeter bonding point area comprising from about 0.01 to about 0.25 mm$^2$. In accordance with certain embodiments of the invention, the plurality of perimeter bonding points may comprise the same or different individual perimeter bonding point area. For example, a set of perimeter bonding points may comprise individual perimeter bonding points having different individual perimeter bonding point areas. Each of the internal bonding points, according to embodiments of the invention, may comprise an individual internal bonding point area comprising from about 0.01 to about 0.25 mm$^2$. In accordance with certain embodiments of the invention, a plurality of internal bonding points may comprise the same or different individual internal bonding point area. For example, a first internal bonding point may comprise a first individual internal bonding area that is different than a second internal bonding point having a second individual internal bonding point area.

In accordance with certain embodiments of the invention, each of the plurality of perimeter bonding points may comprise an individual perimeter bonding point area and each of the internal bonding points may comprise an individual internal bonding point area, in which the individual perimeter bonding point area may be different than the individual internal bonding point area. In according to certain other embodiments of the invention, the individual perimeter bonding point area may be the same as the individual internal bonding point area.

Fabrics according to certain embodiment of the invention include a nonwoven web, in which the nonwoven web comprises a total bond area comprising from about 3% to about 25% of a total area of the nonwoven web. In accordance with certain embodiments of the invention, the nonwoven web may comprise a total bond area comprising from about 5% to about 20% of a total area of the nonwoven web. In accordance with certain such embodiments, the nonwoven web may comprise a total bond area comprising from about 10% to about 18% of a total area of the nonwoven web.

In accordance with certain embodiments of the invention, the one or more internal bonding points being randomly located with the plurality of icons. In certain other embodiments of the invention, however, internal bonding points may define an internal pattern. For example, the internal pattern according to certain embodiments of the invention may comprise any geometric shape, such a circle, a triangle, a square, a rectangle, or a star-shaped pattern. In accordance with certain embodiments of the invention, the internal pattern may be centered within the plurality of icons. In other embodiments of the invention, the internal pattern may not be centered within the plurality of icons. By way of example, each icon of the plurality of icons may each include an internal pattern of internal bonding points either centered or not centered therein. In accordance with certain embodiments of the invention, the plurality of icons include, for example, a third group of icons including a first internal pattern located therein and a fourth group of icons including a second internal pattern located therein, in which the first internal pattern is different than the second internal pattern.

The internal bonding point or points, according to certain embodiments of the invention, may not be located any closer than about 0.25 mm to a nearest perimeter bonding point. In accordance with certain embodiments of the invention, the internal bonding point or points may not be located any closer than about 0.5 mm to a nearest perimeter bonding point. The internal bonding points, according to certain embodiments of the invention, may not be located any closer than about 2 mm to the nearest perimeter bonding point. In accordance with certain embodiments of the invention, the internal bonding point or points may not be located any closer than about 5 mm to a nearest perimeter bonding point. In accordance with certain embodiments of the invention, the internal bonding point or points may not be located any closer than about 8 mm to a nearest perimeter bonding point. In accordance with certain embodiments of the invention, each of the internal bonding points are not located within about 0.2 mm of each other, or within about 0.5 mm of each other, or within about 1 mm of each other.

In accordance with certain embodiments of the invention, the nonwoven web may comprise a single nonwoven layer or a plurality of nonwoven layers. The nonwoven web, according to certain embodiments of the invention, may comprise a spunbond layer. In accordance with certain embodiments of the invention, the nonwoven web may comprise a nonwoven composite comprising, for example, a spunbond layer, a meltblown layer, a carded layer, a hydroentangled layer, or combinations thereof. In one exemplary embodiment of the invention, the nonwoven composite may comprise a spunbond-meltblown-spunbond structure.

In another aspect, the invention provides an embossing roll including a cylindrical base surface area and a plurality of embossing protrusions extending outwardly from the cylindrical base surface and defining an embossing protrusion pattern. In accordance with certain embodiments of the invention, the embossing protrusion pattern may comprising a plurality of icons, in which each of the plurality of icons may be defined by a first group of embossing protrusions comprising a plurality of perimeter embossing protrusions and from 1 to about 5 (e.g., 1 to about 3) internal embossing protrusions located within at least one of the plurality of icons. In certain embodiments of the invention, each of the icons include from 1 to about 5 internal embossing protrusions located therein.

Embossing rolls according to certain embodiments of the invention may comprise a plurality of icons, in which each of the plurality of icons comprise the same geometric shape. In certain other embodiments of the invention, the plurality of icons may comprise two or more different geometric shapes. In this regard, the embossing protrusion pattern, in accordance with certain embodiments of the invention, may comprise a plurality of different geometric shapes. Regardless of whether to plurality of icons of the embossing protrusion pattern are all the same or not, the plurality of icons may each comprise an icon area from about 1 mm$^2$ to about 50 mm$^2$ (e.g., from about 1 mm$^2$ to about 25 mm$^2$). In this regard, each of the plurality of icons may have the same or different icon area. In accordance with certain embodiments of the invention, for example, the plurality of icons may include a first group of icons (e.g., including a first icon) comprising a first icon area and a second group of icons (e.g., including a second icon) comprising a second icon area, in which the first icon area is different than the second icon area. For example, the plurality of icons may comprise a first icon comprising a first icon area and a second icon comprising a second icon area, in which the first icon area is different than the second icon area.

In accordance with certain embodiments of the invention, each of the plurality of perimeter embossing protrusions may comprise an individual perimeter bonding point area comprising from about 0.01 to about 0.25 mm$^2$ and/or a height (dimension extending from the cylindrical base surface) of from about 0.2 mm to about 1.5 mm (e.g., from about 0.2 mm to about 1.0 mm, from about 0.3 mm to about 0.8 mm, from about 0.4 mm to about 0.7 mm). In accordance with certain embodiments of the invention, the plurality of perimeter embossing protrusions may comprise the same or different individual perimeter embossing protrusion area. For example, a set of perimeter embossing protrusions may comprise individual perimeter embossing protrusions having different individual perimeter embossing protrusion areas. Each of the internal embossing protrusions, according to embodiments of the invention, may comprise an individual internal embossing protrusion area comprising from about 0.01 to about 0.25 mm$^2$. In accordance with certain embodiments of the invention, a plurality of internal embossing protrusions may comprise the same or different individual internal embossing protrusion area. For example, a first internal embossing protrusion may comprise a first individual internal embossing protrusion area that is different than a second internal embossing protrusion having a second individual internal bonding point area. In accordance with certain embodiments of the invention, the plurality of perimeter embossing protrusions and the internal embossing protrusions may comprise the same or different height.

In accordance with certain embodiments of the invention, each of the plurality of perimeter embossing protrusions may comprise an individual perimeter embossing protrusion area and each of the internal embossing protrusions may comprise an individual internal embossing protrusion area, in which the individual perimeter embossing protrusion area may be different than the individual internal embossing protrusion area. In according to certain other embodiments of the invention, the individual perimeter embossing protrusion area may be the same as the individual internal embossing protrusion area.

Embossing rolls according to certain embodiments of the invention may include a total embossing protrusion area comprising from about 3% to about 25% of a total area of the embossing roll. In accordance with certain embodiments of the invention, total embossing protrusion area may comprise from about 5% to about 20% of a total area of the embossing roll. In accordance with certain such embodiments, the total embossing protrusion area may comprise from about 10% to about 18% of a total area of the embossing roll.

In accordance with certain embodiments of the invention, the one or more internal embossing protrusions may be randomly located with the plurality of icons. In certain other embodiments of the invention, however, internal embossing protrusions may define an internal pattern. For example, the internal pattern according to certain embodiments of the invention may comprise any geometric shape, such a circle, a triangle, a square, a rectangle, or a star-shaped pattern. In accordance with certain embodiments of the invention, the internal pattern may be centered within the plurality of icons. In other embodiments of the invention, the internal pattern may not be centered within the plurality of icons. By way of example, each icon of the plurality of icons may each include an internal pattern of internal embossing protrusions either centered or not centered therein. In accordance with certain embodiments of the invention, the plurality of icons include, for example, a third group of icons including a first internal pattern located therein and a fourth group of icons including a second internal pattern located therein, in which the first internal pattern is different than the second internal pattern.

The internal embossing protrusion or protrusions, according to certain embodiments of the invention, may not be located any closer than about 0.25 mm to a nearest perimeter embossing protrusion. In accordance with certain embodiments of the invention, the internal embossing protrusion or protrusions may not be located any closer than about 0.5 mm to a nearest perimeter embossing protrusion. The internal embossing protrusion or protrusions, according to certain embodiments of the invention, may not be located any closer than about 2 mm to the nearest perimeter embossing protrusion. In accordance with certain embodiments of the invention, the internal embossing protrusion or protrusions may not be located any closer than about 5 mm to a nearest perimeter embossing protrusion. In accordance with certain embodiments of the invention, the internal embossing protrusion or protrusions may not be located any closer than about 8 mm to a nearest perimeter embossing protrusion. In accordance with certain embodiments of the invention, each of the internal embossing protrusions are not located within about 0.2 mm of each other, or within about 0.5 mm of each other, or within about 1 mm of each other.

In yet another aspect, the invention provides a method of producing an embossed fabric. In accordance with certain embodiments of the invention, the method may comprise a step of directing a nonwoven web into a nip formed between an embossing roll according one or more of the embossing roll embodiments disclosed herein and an anvil roll and imparting an embossed bonding pattern corresponding to the embossing protrusion pattern of the embossing roll. In accordance with certain embodiments of the invention, the embossing roll may comprise an embossing roll material and the anvil roll may comprise an anvil roll material, in which the anvil roll material is softer than the embossing roll material. In accordance with certain embodiments of the invention, the nonwoven web may comprise a single nonwoven layer or a plurality of nonwoven layers. The nonwoven web, according to certain embodiments of the invention, may comprise a spunbond layer. In accordance with certain embodiments of the invention, the nonwoven web may comprise a nonwoven composite comprising, for example, a spunbond layer, a meltblown layer, a carded layer, a hydroentangled layer, or combinations thereof. In one exemplary embodiment of the invention, the nonwoven composite may comprise a spunbond-meltblown-spunbond structure.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

DETAILED DESCRIPTION

Figure 1:
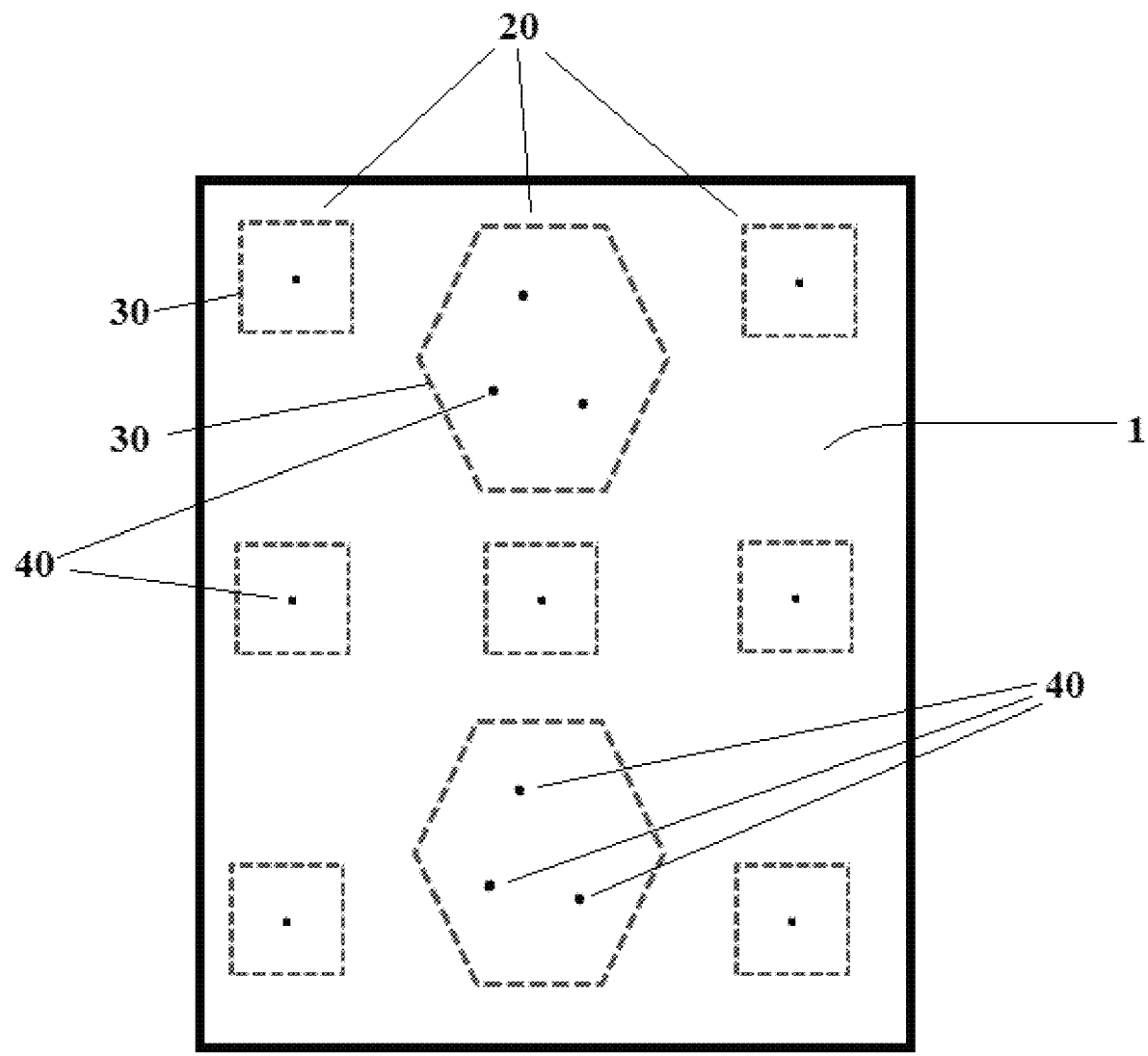
FIG. 1 illustrates an embossed fabric comprising an embossed bonding pattern according to one embodiment of the invention.
Figure 2A:
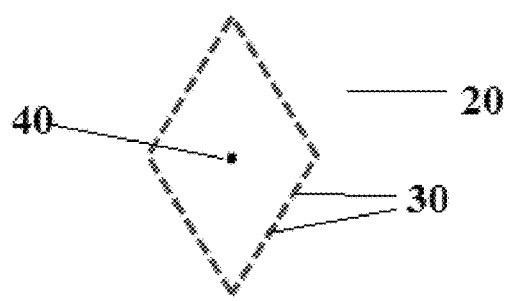
FIGS. 2A-2J illustrate a variety of icon configurations according to certain embodiments of the invention.
Figure 2B:
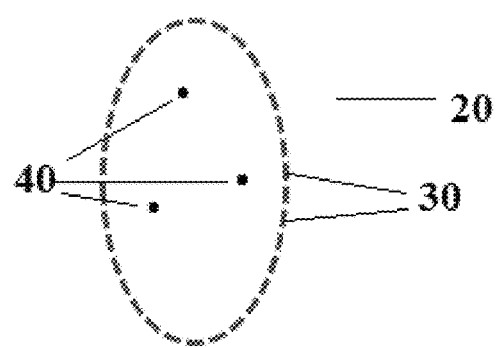
Figure 2C:
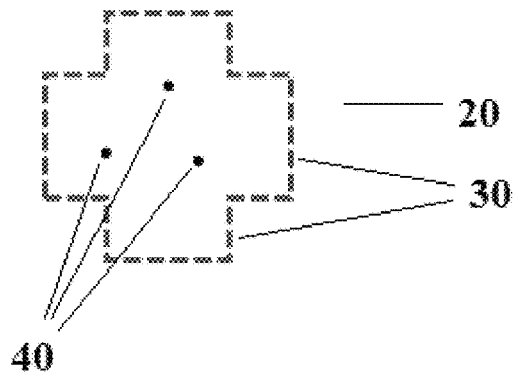
Figure 2D:
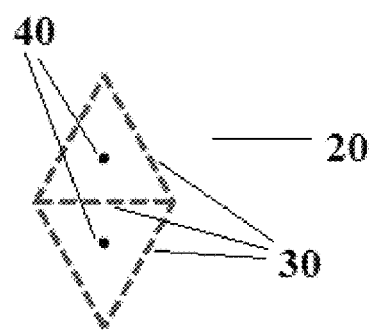
Figure 2E:
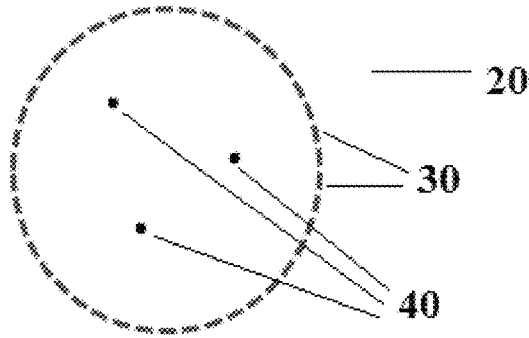
Figure 2F:
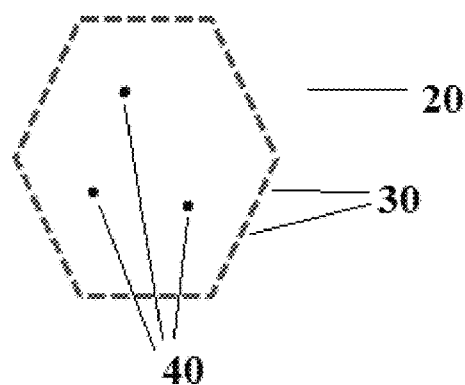
Figure 2G:
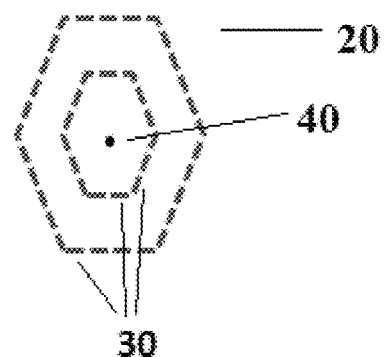
Figure 2H:
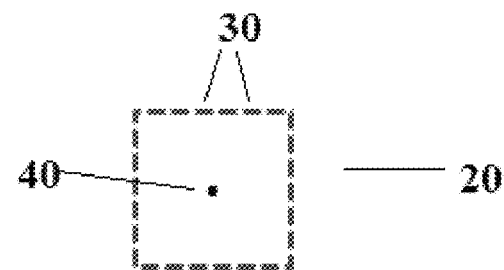
Figure 2I:
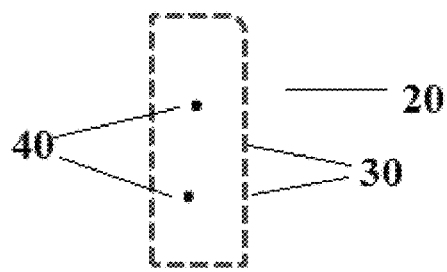
Figure 2J:
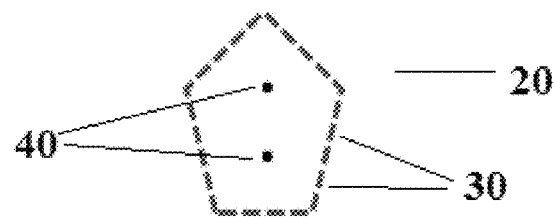

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The invention includes, according to certain embodiments, soft nonwoven fabrics having an embossed bonding pattern thereon. The embossed bonding pattern, according to certain embodiments of the invention, may include a plurality of icons defined by a plurality of perimeter bonding points. The embossed bonding pattern may also include at least one internal bonding point (e.g., from 1 to about 10) located within, for example, each of the plurality of icons. The internal bonding point or points, for instance, may facilitate and/or provide an improved resistance to abrasion and/or linting without sacrificing the level of softness of the embossed fabric.

The terms "substantial" or "substantially" may encompass the whole amount as specified, according to certain embodiments of the invention, or largely but not the whole amount specified according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantionmers; and/or any chiral molecular configuration of such polymer or polymeric material. These configurations include, but are not limited to, isotactic, syndiotactic, and atactic configurations of such polymer or polymeric material. The term "polymer" or "polymeric" shall also include polymers made from various catalyst systems including, without limitation, the Ziegler-Natta catalyst system and the metallocene/single-site catalyst system. The term "polymer" or "polymeric" shall also include polymers produced by fermentation process or biosourced.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, hydroentangling, air-laid, and bonded carded web processes.

The term "layer", as used herein, may comprise a generally recognizable combination of similar material types and/or functions existing in the X-Y plane.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous. It is noted that the spunbond used in certain composites of the invention may include a nonwoven described in the literature as SPIN-LACE®.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers are microfibers which may be continuous or discontinuous and are generally tacky when deposited onto a collecting surface.

The term "hydroentangle" or "hydroentangled", as used herein, may comprise a process for bonding a nonwoven fabric by using high pressure water jets to intermingle the fibers. Several rows of water jets are directed against the fiber web, which is supported by a movable fabric. Fiber entanglements are introduced by the combined effects of the water jets and the turbulent water created in the web, which intertwines neighboring fibers.

The term "laminate", as used herein, may be a structure comprising two or more layers, such as a film layer and a fibrous layer. The two layers of a laminate structure may be joined together such that a substantial portion of their common X-Y plane interface, according to certain embodiments of the invention.

As used herein, the terms "consolidation" and "consolidated" may comprise the bringing together of at least a portion of the fibers of a nonwoven web into closer proximity or attachment there-between (e.g., fused together) to form a bonding site, or bonding sites, which function to increase the resistance of the nonwoven to external forces (e.g., abrasion and tensile forces), as compared to the unconsolidated web. The bonding site or bonding sites, for example, may comprise a discrete or localized region of the web material that has been softened or melted and optionally subsequently or simultaneously compressed to form a discrete or localized deformation in the web material. Furthermore, the term "consolidated" may comprise an entire nonwoven web that has been processed such that at least a portion of the fibers are brought into closer proximity or attachment there-between (e.g., fused together), such as by thermal bonding as merely one example. Such a web may be considered a "consolidated nonwoven" according to certain embodiments of the invention. Additionally, a specific, discrete region of fibers that is brought into close proximity or attachment there-between (e.g., fused together), such as an individual bond site, can be described as "consolidated".

In accordance with certain embodiments of the invention, consolidation may be achieved by methods that apply, for example, heat and/or pressure to the fibrous web (e.g., nonwoven web) via one or more embossing rolls. One non-limiting and exemplary method comprises thermal bonding. Thermal bonding can be accomplished by passing the fibrous web (e.g., nonwoven web) through a pressure nip formed by two rolls, one of which comprising an embossing roll which may be heated and contain a plurality of raised protrusions having one or more geometric shapes (e.g., points, diamond shaped, circular, elliptical, dog-bone shaped, etc.) on its surface which impart or form corresponding discrete thermal bond sites on the fibrous web (e.g., nonwoven web). Such an operating step, for example, may be referred to as "calendaring" or "embossing" in which the nonwoven web is drawn between an embossing roll having an embossing pattern allowing only part of the web to become exposed to heat and pressure and a second roll (e.g., an anvil roll). The degree or extent of consolidation may be expressed as a percentage of the total surface area of the web that has been consolidated or subjected to consolidation and may be referred to as a "bonding area" or "consolidation area". Stated somewhat differently, the terms "bonding area" and "consolidated area", as used interchangeably herein, may comprise the area per unit area occupied by the localized sites formed by bonding the fibers into bond sites and may be expressed as a percentage of the total unit area of the consolidated nonwoven. For example, consolidated nonwovens (e.g., subjected to thermal bonding via an embossing roll) may comprise a plurality of discrete, spaced-apart bond sites or points (e.g., perimeter and internal bond sites or points) formed by bonding only the fibers of the nonwoven web in the area of localized energy input. Fibers or portions of fibers remote from the localized energy input remain substantially unbonded to adjacent fibers.

The term "icon", as used herein, may comprise a single, discrete, design or geometric shape being defined by, at least partially, a plurality of bonding points (e.g., a plurality of perimeter bonding points). For example, an icon may comprise a caricature (e.g., an animal, flower, logo, etc.) or other design. In certain embodiments of the invention, an icon may, for example, may comprise a variety of geometric shapes including triangles, squares, rectangles, circles, ovals, arcs, stars, or combinations thereof.

The term "bicomponent fibers", as used herein, may comprise fibers formed from at least two different polymers extruded from separate extruders but spun together to form one fiber. Bicomponent fibers are also sometimes referred to as conjugate fibers or multicomponent fibers. The polymers are arranged in a substantially constant position in distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement, each as is known in the art of multicomponent, including bicomponent, fibers. The "bicomponent fibers" may be thermoplastic fibers that comprise a core fiber made from one polymer that is encased within a thermoplastic sheath made from a different polymer or have a side-by-side arrangement of different thermoplastic fibers. The first polymer often melts at a different, typically lower, temperature than the second polymer. In the sheath/core arrangement, these bicomponent fibers provide thermal bonding due to melting of the sheath polymer, while retaining the desirable strength characteristics of the core polymer. In the side-by-side arrangement, the fibers shrink and crimp creating z-direction expansion.

The terms "lint" and "lint level", as used herein, may comprise the tendency of a web to shed particles when manipulated. This tendency may be measured in accordance to the standard test method WSP 400.0 (05).

I. Embossed Fabrics

In one aspect, the invention provides fabrics comprising a nonwoven web including an embossed bonding pattern. The embossed bonding pattern, according to certain embodiments of the invention, may comprise a plurality of icons, in which each of the plurality of icons may be defined by a plurality of perimeter bonding points and from 1 to about 5 (e.g., 1-3) internal bonding points located within at least one of the plurality of icons. In certain embodiments of the invention, each of the icons include from 1 to about 5 internal bonding points located therein. In accordance with certain embodiments of the invention, the number of internal bonding points within a given icon may comprise from 1 to about 10 (e.g., 1, 2, 3, 4, 5, 6, 7, 8, 9, or 10) discrete internal bonding points.

Fabrics according to certain embodiments of the invention may comprise a plurality of icons, in which each of the plurality of icons comprise the same geometric shape. In certain other embodiments of the invention, the plurality of icons may comprise two or more different geometric shapes (e.g., an oval and a square). In this regard, the embossed bonding pattern of fabrics, in accordance with certain embodiments of the invention, may comprise a plurality of different geometric shapes as described above. Regardless of whether to plurality of icons of the embossed bonding pattern are all the same or not, the plurality of icons may each independently comprise an icon area from about 1 mm$^2$ to about 50 mm$^2$ (e.g., from about 1 mm$^2$ to about 25 mm$^2$). In accordance with certain embodiments of the invention, the plurality of icons may each independently comprise an icon area from at least about any of the following: 1 mm$^2$, 5 mm$^2$, 10 mm$^2$, 15 mm$^2$, 20 mm$^2$ and 25 mm$^2$ and/or at most about 50 mm$^2$, 45 mm$^2$, 40 mm$^2$, 35 mm$^2$, 30 mm$^2$ and 25 mm$^2$ (e.g., about 1-25 mm$^2$, about 10-35 mm$^2$, etc.). In this regard, each of the plurality of icons may have the same or different icon area. In accordance with certain embodiments of the invention, for example, the plurality of icons may include a first group of icons (e.g., including a first icon) comprising a first icon area and a second group of icons (e.g., including a second icon) comprising a second icon area, in which the first icon area is different than the second icon area. For example, the plurality of icons may comprise a first icon comprising a first icon area and a second icon comprising a second icon area, in which the first icon area is different than the second icon area.

FIG. 1, for example, illustrates an embossed fabric according to one example embodiment of the invention. The particular embodiment of the invention illustrated by FIG. 1 shows an embossed nonwoven fabric 1 includes embossed bonding pattering comprising a plurality of icons 20. Each of the plurality of icons is defined by several perimeter bonding points 30. As shown in FIG. 1, a single embossed nonwoven fabric 1 may comprise a plurality of icons 20 including differing geometric shapes. For example, the fabric 1 of FIG. 1 includes a first group of icons 20 having a square geometric shape and a second group of icons 20 having a hexagonal geometric shape. FIG. 1 also illustrates an exemplary embodiment in which each of the icons 20 include either one (1) or three (3) separate and discrete internal bonding points 40 located within the icons 20. In this regard, the internal bonding points 40 are generally circumscribed by the plurality of perimeter bonding points 30 of each icon. Additionally, FIG. 1 illustrates that some of the icons 20 (i.e., the square-shaped icons) include centered internal bonding point 40 while other icons (i.e., the hexagonal-shaped icons) do not.

In accordance with certain embodiments of the invention, the plurality of icons may comprise a variety of different geometric shapes. By way of example, FIGS. 2A through 2J illustrate a variety of icon configurations according to certain embodiments of the invention. In this regard, an embossed fabric according to certain embodiments of the invention may comprise one or more of the icons illustrated by FIGS. 2A through 2J.

In accordance with certain embodiments of the invention, each of the plurality of perimeter bonding points may comprise an individual perimeter bonding point area comprising from about 0.01 to about 0.25 mm$^2$. In accordance with certain embodiments of the invention, the plurality of perimeter bonding points may comprise the same or different individual perimeter bonding point area. For example, a set of perimeter bonding points may comprise individual perimeter bonding points having different individual perimeter bonding point areas. In accordance with certain embodiments of the invention, each of the plurality of perimeter bonding points may independently comprise an individual perimeter bonding point area from at least about any of the following: 0.01 mm$^2$, 0.05 mm$^2$, 0.1 mm$^2$, 0.15 mm$^2$, and 0.2 mm$^2$ and/or at most about 0.5 mm$^2$, 0.45 mm$^2$, 0.4 mm$^2$, 0.35 mm$^2$, 0.3 mm$^2$ and 0.25 mm$^2$ (e.g., about 0.1-0.25 mm$^2$, about 0.01-0.5 mm$^2$, etc.).

Each of the internal bonding points, according to embodiments of the invention, may comprise an individual internal bonding point area comprising from about 0.01 to about 0.25 mm$^2$. In accordance with certain embodiments of the invention, a plurality of internal bonding points may comprise the same or different individual internal bonding point area. For example, a first internal bonding point may comprise a first individual internal bonding area that is different than a second internal bonding point having a second individual internal bonding point area. In accordance with certain embodiments of the invention, each of the internal bonding points may independently comprise an individual internal bonding point area from at least about any of the following: 0.01 mm$^2$, 0.05 mm$^2$, 0.1 mm$^2$, 0.15 mm$^2$, and 0.2 mm$^2$ and/or at most about 0.5 mm$^2$, 0.45 mm$^2$, 0.4 mm$^2$, 0.35 mm$^2$, 0.3 mm$^2$ and 0.25 mm$^2$ (e.g., about 0.1-0.25 mm$^2$, about 0.01-0.5 mm$^2$, etc.).

In accordance with certain embodiments of the invention, each of the plurality of perimeter bonding points may comprise an individual perimeter bonding point area and each of the internal bonding points may comprise an individual internal bonding point area, in which the individual perimeter bonding point area may be different than the individual internal bonding point area. In according to certain other embodiments of the invention, the individual perimeter bonding point area may be the same as the individual internal bonding point area.

Fabrics according to certain embodiment of the invention may include a nonwoven web, in which the nonwoven web comprises a total bond area comprising from about 3% to about 25% of a total area of the nonwoven web. In accordance with certain embodiments of the invention, the nonwoven web may comprise a total bond area comprising from about 5% to about 20% of a total area of the nonwoven web. In accordance with certain such embodiments, the nonwoven web may comprise a total bond area comprising from about 10% to about 18% of a total area of the nonwoven web. For example, in certain embodiments of the invention, the nonwoven web may comprise a total bond area comprising from at least about any of the following: 1, 2, 3, 5, 8, and 10% of a total area of the nonwoven web and/or at most about 30, 25, 20, 18, 15, 12, and 10% of a total area of the nonwoven web (e.g., about 2-20% of a total area of the nonwoven web, about 10-15% of a total area of the nonwoven web, etc.).

In accordance with certain embodiments of the invention, the one or more internal bonding points may be randomly located with the plurality of icons. In certain other embodiments of the invention, however, internal bonding points may define an internal pattern. For example, the internal pattern according to certain embodiments of the invention may comprise any geometric shape, such a circle, a triangle, a square, a rectangle, or a star-shaped pattern. In accordance with certain embodiments of the invention, the internal pattern may be centered within the plurality of icons. In other embodiments of the invention, the internal pattern may not be centered within the plurality of icons. By way of example, each icon of the plurality of icons may each include an internal pattern of internal bonding points either centered or not centered therein. In accordance with certain embodiments of the invention, the plurality of icons include, for example, a third group of icons including a first internal pattern located therein and a fourth group of icons including a second internal pattern located therein, in which the first internal pattern is different than the second internal pattern.

The internal bonding point or points, according to certain embodiments of the invention, may not be located any closer than about 0.25 mm to a nearest perimeter bonding point. In accordance with certain embodiments of the invention, the internal bonding point or points may not be located any closer than about 0.5 mm to a nearest perimeter bonding point. The internal bonding points, according to certain embodiments of the invention, may not be located any closer than about 2 mm to the nearest perimeter bonding point. In accordance with certain embodiments of the invention, the internal bonding point or points may not be located any closer than about 5 mm to a nearest perimeter bonding point. In accordance with certain embodiments of the invention, the internal bonding point or points may not be located any closer than about 8 mm to a nearest perimeter bonding point. In accordance with certain embodiments of the invention, each of the internal bonding points are not located within about 0.2 mm of each other, or within about 0.5 mm of each other, or within about 1 mm of each other.

In accordance with certain embodiments of the invention, the nonwoven web may comprise a single nonwoven layer or a plurality of nonwoven layers. The nonwoven web, according to certain embodiments of the invention, may comprise a spunbond layer. In accordance with certain embodiments of the invention, the nonwoven web may comprise a nonwoven composite comprising, for example, a spunbond layer, a meltblown layer, a carded layer, a hydroentangled layer, or combinations thereof. In one exemplary embodiment of the invention, the nonwoven composite may comprise a spunbond-meltblown-spunbond structure. According to certain embodiments of the invention, for example, the nonwoven web may comprise a plurality of nonwoven webs (e.g., a laminate or composite). Exemplary configurations include, but are not limited to, $S_1S_1S_2$, $S_1S_1S_2S_2$, and $S_1S_2 \ S_2$, where $S_1$=a first nonwoven web structure and $S_2$=a second nonwoven web structure. In further embodiments, for instance, one or more meltblown and/or submicron-fiber-containing layer may be located directly or indirectly between any two of the spunbond layers. For example, the nonwoven web, as noted above, may comprise an SMS configuration, where S=spunbond and M=meltblown.

In accordance with certain embodiments of the invention, one or more of the layers of the nonwoven web may comprise a variety of synthetic or natural polymeric materials. For example, the nonwoven web may comprise a spunbond layer including a polypropylene, such as an isotactic polypropylene. In certain embodiments of the invention, for example, the spunbond may comprise a a polyrpopylen, polyethylene, or both. In such embodiments of the invention, for instance, the spunbond may comprise high density polypropylene or high density polyethylene, low density polypropylene or low density polyethylene, linear low density polypropylene or linear low density polyethylene, a copolymer of polypropylene or ethylene, and any combination thereof. In some embodiments of the invention, the nonwoven web (e.g., a spunbond layer) may comprise at least one of a polypropylene, a polyethylene, a polyester, a polyamide, or combinations thereof. In accordance with certain embodiments of the invention, the nonwoven web may comprise one or more layers comprising a biopolymer (e.g., polylactic acid (PLA) polyhydroxyalkanoates (PHA), and poly(hydroxycarboxylic) acids). In accordance with certain embodiments of the invention, the nonwoven web may comprise an interior layer comprising a biopolymer being sandwiched, either directly or indirectly, between two spunbond layers.

In accordance with certain embodiments of the invention, the nonwoven web may comprise one or more individual layers, in which one or more of the individual layers include multi-component fibers, such as bicomponent fibers having a sheath-core configuration. For example, certain embodiments of the invention may comprise bicomponent fibers comprising a sheath comprising, by way of example only, a polyethylene or a propylene and a core comprising, by way of example only, at least one of a polypropylene, a polyethylene, a polyester, or a biopolymer (e.g., polylactic acid (PLA) polyhydroxyalkanoates (PHA), and poly(hydroxycarboxylic) acids.

II. Embossing Rolls

In another aspect, the invention provides an embossing roll including a cylindrical base surface area and a plurality of embossing protrusions extending outwardly from the cylindrical base surface and defining an embossing protrusion pattern. In accordance with certain embodiments of the invention, the embossing protrusion pattern may comprising a plurality of icons, in which each of the plurality of icons may be defined by a first group of embossing protrusions comprising a plurality of perimeter embossing protrusions and from 1 to about 5 (e.g., 1 to about 3) internal embossing protrusions located within at least one of the plurality of icons. In certain embodiments of the invention, each of the icons include from 1 to about 10 (e.g., 1, 2, 3, 4, 5, 6, 7, 8, 9, or 10) internal embossing protrusions located therein.

Embossing rolls according to certain embodiments of the invention may comprise a plurality of icons, in which each of the plurality of icons comprise the same geometric shape. In certain other embodiments of the invention, the plurality of icons may comprise two or more different geometric shapes (e.g., an oval and a square). In this regard, the embossing protrusion pattern, in accordance with certain embodiments of the invention, may comprise a plurality of different geometric shapes. Regardless of whether to plurality of icons of the embossing protrusion pattern are all the same or not, the plurality of icons may each comprise an icon area from about 1 mm² to about 50 mm² (e.g., from about 1 mm² to about 25 mm²). In accordance with certain embodiments of the invention, the plurality of icons may each independently comprise an icon area from at least about any of the following: 1 mm², 5 mm², 10 mm², 15 mm², 20 mm² and 25 mm² and/or at most about 50 mm², 45 mm², 40 mm², 35 mm², 30 mm² and 25 mm² (e.g., about 1-25 mm², about 10-35 mm², etc.). In this regard, each of the plurality of icons may have the same or different icon area. In accordance with certain embodiments of the invention, for example, the plurality of icons may include a first group of icons (e.g., including a first icon) comprising a first icon area and a second group of icons (e.g., including a second icon) comprising a second icon area, in which the first icon area is different than the second icon area. For example, the plurality of icons may comprise a first icon comprising a first icon area and a second icon comprising a second icon area, in which the first icon area is different than the second icon area.

Figure 3:
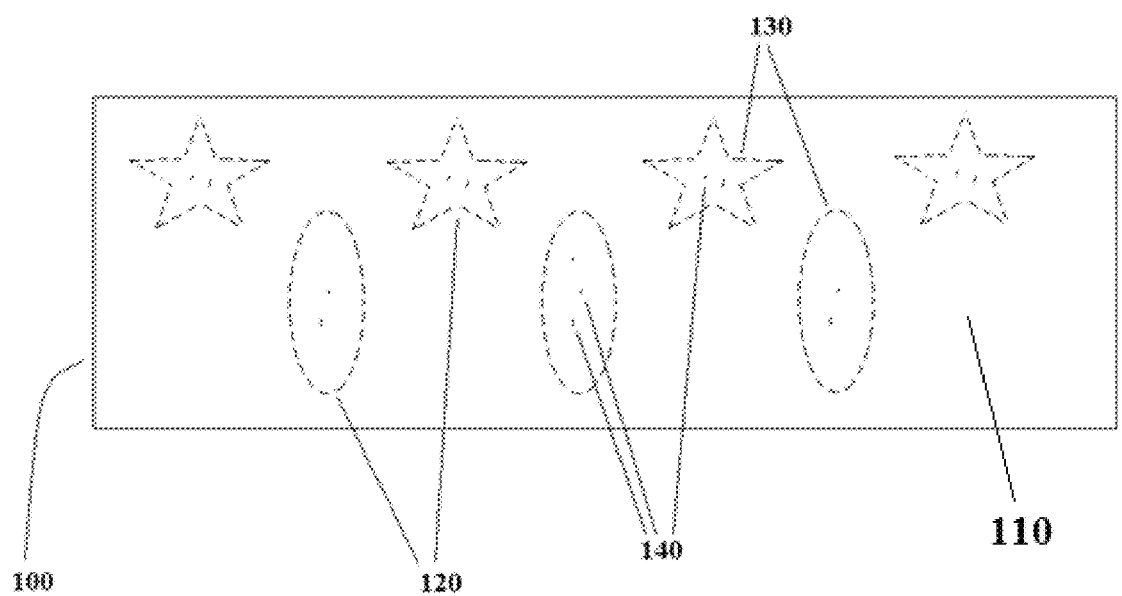
FIG. 3 illustrates a embossing roll including a plurality of embossing protrusions defining an embossing protrusion pattern, including a plurality of icons, according to an embodiment of the invention.

FIG. 3, for example, illustrates an embossing roll 100 having a cylindrical base surface area 110 and a plurality of embossing protrusions 130, 140 extending outwardly from the cylindrical base surface area 110. As illustrated by FIG. 3, the embossing roll may include a plurality of icons 120 defined by a first group of embossing protrusions comprising a plurality of perimeter embossing protrusions 130. FIG. 3 also illustrates an embodiment of the invention including internal embossing protrusions 140 located within each of the icons 120. The particular embodiment illustrated by FIG. 3, includes some icons 120 including three internal protrusions 140 while other icons 120 within the same pattern have two internal protrusions 130. In this regard, embossing protrusion patterns according to embodiments of the invention can include a variety of different or identical geometric shapes such as those illustrated (for example) by FIG. 2A through FIG. 2J, while the number of internal embossing protrusions within in some or each of the icons of the embossing protrusion pattern may independently vary as described herein.

In accordance with certain embodiments of the invention, each of the plurality of perimeter embossing protrusions may comprise an individual perimeter bonding point area comprising from about 0.01 to about 0.25 mm² and/or a height (dimension extending from the cylindrical base surface) of from about 0.2 mm to about 1.5 mm (e.g., from about 0.2 mm to about 1.0 mm, from about 0.3 mm to about 0.8 mm, from about 0.4 mm to about 0.7 mm). In accordance with certain embodiments of the invention, the plurality of perimeter embossing protrusions may comprise the same or different individual perimeter embossing protrusion area. For example, a set of perimeter embossing protrusions may comprise individual perimeter embossing protrusions having different individual perimeter embossing protrusion areas. In accordance with certain embodiments of the invention, each of the plurality of perimeter embossing protrusion may independently comprise an individual perimeter embossing protrusion area from at least about any of the following: 0.01 mm², 0.05 mm², 0.1 mm², 0.15 mm², and 0.2 mm² and/or at most about 0.5 mm², 0.45 mm², 0.4 mm², 0.35 mm², 0.3 mm² and 0.25 mm² (e.g., about 0.1-0.25 mm², about 0.01-0.5 mm², etc.). In accordance with certain embodiments of the invention, each of the plurality of perimeter embossing protrusion may independently comprise an individual height (dimension extending from the cylindrical base surface) of from at least about any of the following: 0.1 mm, 0.2 mm, 0.3 mm, 0.4 mm, and 0.5 mm and/or at most about 1.5 mm, 1.25 mm, 1.0 mm, 0.8 mm, and 0.7 mm (e.g., about 0.1-0.8 mm, about 0.4-0.7 mm, etc.).

Each of the internal embossing protrusions, according to embodiments of the invention, may comprise an individual internal embossing protrusion area comprising from about 0.01 to about 0.25 mm². In accordance with certain embodiments of the invention, a plurality of internal embossing protrusions may comprise the same or different individual internal embossing protrusion area. For example, a first internal embossing protrusion may comprise a first individual internal embossing protrusion area that is different than a second internal embossing protrusion having a second individual internal bonding point area. In accordance with certain embodiments of the invention, the plurality of perimeter embossing protrusions and the internal embossing protrusions may comprise the same or different height. In accordance with certain embodiments of the invention, each of the internal embossing protrusion(s) may independently comprise an individual internal embossing protrusion area from at least about any of the following: 0.01 mm², 0.05 mm², 0.1 mm², 0.15 mm², and 0.2 mm² and/or at most about 0.5 mm², 0.45 mm², 0.4 mm², 0.35 mm², 0.3 mm² and 0.25 mm² (e.g., about 0.1-0.25 mm², about 0.01-0.5 mm², etc.). In accordance with certain embodiments of the invention, each of the internal embossing protrusion(s) may independently comprise an individual height (dimension extending from the cylindrical base surface) of from at least about any of the following: 0.1 mm, 0.2 mm, 0.3 mm, 0.4 mm, and 0.5 mm and/or at most about 1.5 mm, 1.25 mm, 1.0 mm, 0.8 mm, and 0.7 mm (e.g., about 0.1-0.8 mm, about 0.4-0.7 mm, etc.).

In accordance with certain embodiments of the invention, each of the plurality of perimeter embossing protrusions may comprise an individual perimeter embossing protrusion area and each of the internal embossing protrusions may comprise an individual internal embossing protrusion area, in which the individual perimeter embossing protrusion area may be different than the individual internal embossing protrusion area. In according to certain other embodiments of the invention, the individual perimeter embossing protrusion area may be the same as the individual internal embossing protrusion area.

Embossing rolls according to certain embodiments of the invention may include a total embossing protrusion area comprising from about 3% to about 25% of a total area of the embossing roll (e.g. a sum of the base surface area and the total embossing protrusion area). In accordance with certain embodiments of the invention, total embossing protrusion area may comprise from about 5% to about 20% of a total area of the embossing roll. In accordance with certain such embodiments, the total embossing protrusion area may comprise from about 10% to about 18% of a total area of the embossing roll. For example, in certain embodiments of the invention, the embossing roll may comprise a total embossing protrusion area comprising from at least about any of the following: 1, 2, 3, 5, 8, and 10% of a total area of the embossing roll and/or at most about 30, 25, 20, 18, 15, 12, and 10% of a total area of the embossing roll (e.g., about 2-20% of a total area of the embossing roll, about 10-15% of a total area of the embossing roll, etc.).

In accordance with certain embodiments of the invention, the one or more internal embossing protrusions may be randomly located with the plurality of icons. In certain other embodiments of the invention, however, internal embossing protrusions may define an internal pattern. For example, the internal pattern according to certain embodiments of the invention may comprise any geometric shape, such a circle, a triangle, a square, a rectangle, or a star-shaped pattern. In accordance with certain embodiments of the invention, the internal pattern may be centered within the plurality of icons. In other embodiments of the invention, the internal pattern may not be centered within the plurality of icons. By way of example, each icon of the plurality of icons may each include an internal pattern of internal embossing protrusions either centered or not centered therein. In accordance with certain embodiments of the invention, the plurality of icons include, for example, a third group of icons including a first internal pattern located therein and a fourth group of icons including a second internal pattern located therein, in which the first internal pattern is different than the second internal pattern.

The internal embossing protrusion or protrusions, according to certain embodiments of the invention, may not be located any closer than about 0.25 mm to a nearest perimeter embossing protrusion. In accordance with certain embodiments of the invention, the internal embossing protrusion or protrusions may not be located any closer than about 0.5 mm to a nearest perimeter embossing protrusion. The internal embossing protrusion or protrusions, according to certain embodiments of the invention, may not be located any closer than about 2 mm to the nearest perimeter embossing protrusion. In accordance with certain embodiments of the invention, the internal embossing protrusion or protrusions may not be located any closer than about 5 mm to a nearest perimeter embossing protrusion. In accordance with certain embodiments of the invention, the internal embossing protrusion or protrusions may not be located any closer than about 8 mm to a nearest perimeter embossing protrusion. In accordance with certain embodiments of the invention, each of the internal embossing protrusions are not located within about 0.2 mm of each other, or within about 0.5 mm of each other, or within about 1 mm of each other.

III. Methods of Producing an Embossed Fabric

In yet another aspect, the invention provides a method of producing an embossed fabric. In accordance with certain embodiments of the invention, the method may comprise a step of directing a nonwoven web into a nip formed between an embossing roll according one or more of the embossing roll embodiments disclosed herein and, for example, an anvil roll and imparting an embossed bonding pattern corresponding to the embossing protrusion pattern of the embossing roll. In accordance with certain embodiments of the invention, the embossing roll may comprise an embossing roll material and the anvil roll may comprise an anvil roll material, in which the anvil roll material is softer than the embossing roll material.

In accordance with certain embodiments of the invention, the nonwoven web may comprise a single nonwoven layer or a plurality of nonwoven layers. The nonwoven web, according to certain embodiments of the invention, may comprise a spunbond layer. In accordance with certain embodiments of the invention, the nonwoven web may comprise a nonwoven composite comprising, for example, a spunbond layer, a meltblown layer, a carded layer, a hydroentangled layer, or combinations thereof. In one exemplary embodiment of the invention, the nonwoven composite may comprise a spunbond-meltblown-spunbond structure. According to certain embodiments of the invention, for example, the nonwoven web may comprise a plurality of nonwoven webs (e.g., a laminate or composite). Exemplary configurations include, but are not limited to, $S_1S_1S_2$, $S_1S_1S_2S_2$, and $S_1S_2\ S_1$, where $S_1$=a first nonwoven web structure and $S_2$=a second nonwoven web structure. In further embodiments, for instance, one or more meltblown and/or submicron-fiber-containing layer may be located directly or indirectly between any two of the spunbond layers. For example, the nonwoven web, as noted above, may comprise an SMS configuration, where S=spunbond and M=meltblown.

In accordance with certain embodiments of the invention, one or more of the layers of the nonwoven web may comprise a variety of synthetic or natural polymeric materials. For example, the nonwoven web may comprise a spunbond layer including a polypropylene, such as an isotactic polypropylene. In certain embodiments of the invention, for example, the spunbond may comprise a a polyrpopylen, polyethylene, or both. In such embodiments of the invention, for instance, the spunbond may comprise high density polypropylene or high density polyethylene, low density polypropylene or low density polyethylene, linear low density polypropylene or linear low density polyethylene, a copolymer of polypropylene or ethylene, and any combination thereof. In some embodiments of the invention, the nonwoven web (e.g., a spunbond layer) may comprise at least one of a polypropylene, a polyethylene, a polyester, a polyamide, or combinations thereof. In accordance with certain embodiments of the invention, the nonwoven web may comprise one or more layers comprising a biopolymer (e.g., polylactic acid (PLA) polyhydroxyalkanoates (PHA), and poly(hydroxycarboxylic) acids). In accordance with certain embodiments of the invention, the nonwoven web may comprise an interior layer comprising a biopolymer being sandwiched, either directly or indirectly, between two spunbond layers.

In accordance with certain embodiments of the invention, the nonwoven web may comprise one or more individual layers, in which one or more of the individual layers include multi-component fibers, such as bicomponent fibers having a sheath-core configuration. For example, certain embodiments of the invention may comprise bicomponent fibers comprising a sheath comprising, by way of example only, a polyethylene or a propylene and a core comprising, by way of example only, at least one of a polypropylene, a polyethylene, a polyester, or a biopolymer (e.g., polylactic acid (PLA) polyhydroxyalkanoates (PHA), and poly(hydroxycarboxylic) acids.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A fabric, comprising:
   a nonwoven web comprising an embossed bonding pattern,
   the embossed bonding pattern comprising (i) a plurality of icons, each of the plurality of icons being defined by a plurality of perimeter bonding points and (ii) a plurality of internal bonding points located within at least one of the plurality of icons; the plurality of internal bonding points consisting of 2, 3, 4, or 5 individual internal bonding points; the plurality of icons includes a first discrete icon comprising a first plurality of perimeter bonding points and a second discrete icon comprising a second plurality of perimeter bonding points;

wherein each of the first plurality of perimeter bonding points is separate and distinct from each of the second plurality of perimeter bonding points wherein the nonwoven web has a total bond area from 3% to 18%.

2. The fabric according to claim 1, wherein the plurality of icons each comprise an icon area from 1 mm² to 50 mm².

3. The fabric according to claim 1, wherein the first discrete icon comprises a first icon area and the second discrete icon comprises a second icon area; wherein the first icon area is larger than the second icon area.

4. The fabric according to claim 1, wherein each of the plurality of perimeter bonding points comprises an individual perimeter bonding point area comprising from 0.01 to 0.25 mm² and wherein each of the individual internal bonding points comprise an individual internal bonding point area comprising from 0.01 to 0.25 mm².

5. The fabric according to claim 1, wherein each of the plurality of perimeter bonding points comprise an individual perimeter bonding point area and each of the individual internal bonding points comprise an individual internal bonding point area; wherein the individual perimeter bonding point area is different than the individual internal bonding point area.

6. The fabric according to claim 1, wherein each of the icons has 2 or 3 individual internal bonding points.

7. The fabric according to claim 1, wherein the nonwoven web comprises a total bond area comprising from 10% to 18% of a total area of the nonwoven web.

8. The fabric according to claim 1, wherein the individual internal bonding points are randomly located with the plurality of icons.

9. The fabric according to claim 1, wherein internal bonding points define an internal pattern.

10. The fabric according to claim 9, wherein the internal pattern is centered within the plurality of icons.

11. The fabric according to claim 9, wherein the internal pattern is not centered within the plurality of icons.

12. The fabric according to claim 1, wherein the individual internal bonding points are located no closer than 0.25 mm to a nearest perimeter bonding point.

13. The fabric according to claim 1, wherein the nonwoven web comprises a spunbond layer.

14. The fabric according to claim 1, wherein the internal bonding points are located no closer than 5 mm to a nearest perimeter bonding point.

15. The fabric according to claim 1, wherein the embossed bonding pattern has from 2 to 5 first internal bonding points circumscribed by the first plurality of perimeter bonding points and from 2 to 5 second internal bonding points circumscribed by the second plurality of perimeter bonding points.

16. A fabric, comprising an embossed pattern including (i) a first icon being defined by a first plurality of perimeter bonding points and defining a first icon shape; (ii) a second icon being defined by a second plurality of perimeter bonding points and defining a second icon shape; wherein the first icon shape is different than the second icon shape; (iii) one or more first-internal bonding points consisting of 1, 2, 3, 4, or 5 individual first internal bonding points located within the first plurality of perimeter bonding points; wherein the 1, 2, 3, 4, or 5 individual first internal bonding points are not centrally located within first plurality of perimeter bonding points; and (iv) one or more second-internal bonding points consisting of 1, 2, 3, 4, or 5 individual second internal bonding points located within the second plurality of perimeter bonding points; wherein the 1, 2, 3, 4, or 5 individual second internal bonding points are either centrally located within first plurality of perimeter bonding points or not centrally located within first plurality of perimeter bonding points; wherein the nonwoven web has a total bond area from 3% to 18%.

17. The fabric of claim 16, wherein the second icon has only one individual second internal bonding point located therein.

18. The fabric according to claim 1, wherein the individual internal bonding points are located within 0.2 mm to 1 mm from each other.

* * * * *